US006126839A

United States Patent [19]
Kreader et al.

[11] Patent Number: 6,126,839
[45] Date of Patent: Oct. 3, 2000

[54] USE OF AN ALCOHOL-SALT BUFFER WASH FOR THE EFFICIENT RECOVERY OF MYCOBACTERIA AND MYCOBACTERIAL DNA FROM RESPIRATORY SEDIMENT

[76] Inventors: Carol Kreader, 114 Fairview Cir., Webster, N.Y. 14580; John W. Backus, 12865 Via Caballo Rojo, San Diego, Calif. 92129; Joanne H. Kerschner, 9033 Clayton Rd., St. Louis, Mo. 63117; Rashmi Mehta, 122 Machado Cove, Dona Paula, Goa, India

[21] Appl. No.: 09/013,987

[22] Filed: Jan. 27, 1998

Related U.S. Application Data

[60] Provisional application No. 60/039,239, Feb. 28, 1997.
[51] Int. Cl.[7] .......................... B01D 21/26; B01D 21/01; C12N 1/00
[52] U.S. Cl. ......................... 210/724; 210/723; 210/725; 210/728; 210/729; 210/787; 210/789; 435/6; 435/243; 435/253.1
[58] Field of Search ..................................... 210/634, 723, 210/724, 725, 728, 729, 781, 782, 789, 787; 435/2, 6, 243, 253.1, 260, 261; 436/177, 178

[56] References Cited

FOREIGN PATENT DOCUMENTS

| 0 285 439 A2 | 5/1988 | European Pat. Off. . |
| 0 626 456 A1 | 11/1994 | European Pat. Off. . |
| 94917192 | 1/1998 | European Pat. Off. . |

OTHER PUBLICATIONS

Beavis, K.G. et al.; Evaluation of Amplicor PCR for Direct Detection of *Mycobacterium tuberculosis* from Sputum Specimens; Journal of Clinical Microbiology, Oct., 1995, p. 2582–2586.
Williams, D.L. et al.; Ethanol Fixation of Sputum Sediments for DNS–Based Detection of *Mycobacterium tuberculosis;* Journal of Clinical Microbiology, Jun. 1995, p. 1558–1561.
Best, M. et al.; Efficacies of Selected Disinfectants against *Mycobacterium tuberculosis;* Journal of Clinical Microbiology, Oct., 1990, p. 2234–2239.
Lind, A., et al.; A carrier method for the assessment of the effectiveness of disinfectants against *Mycobacterium tuberculosis;* Journal of Hospital Infection (1986) 7, 60–67.

Kent, P.T., et al.; Public Health Mycobacteriology A Guide for the Level III Laboratory; U.S. Dept. of Health and Human Services Public Health Service Centers for Disease Control, 1985, p. 31–47.
Noordhoek, G.T., et al.; Sensitivity and Specificity of PCR for Detection of *Mycobacterium tuberculosis:* a Blind Comparison Study among Seven Laboratories; Journal of Clinical Microbiology, Feb. 1994, p. 277–284.
Nolte, F.S. et al.; Direct Detection of *Mycobacterium tuberculosis* in Sputum by Polymerase Chain Reaction and DNA Hybridization; Journal of Clinical Microbiology, Jul. 1993, p. 1777–1782.
Forbes, B.A. et al.; Direct Detection of *Mycobacterium tuberculosis* in Respiratory Specimens in a Clinical Laboratory by Polymerase Chain Reaction; Journal of Clinical Microbiology, Jul. 1993, p. 1688–1694.
Hurley, S.S. et al.; Rapid Lysis Technique for Mycobacterial Species; Journal of Clinical Microbiology, Nov. 1987, p. 2227–2229.
Buck, G.E., et al.; Rapid, Simple Method for Treating Clinical Specimens Containing *Mycobacterium tuberculosis* To Remove DNA for Polymerase Chain Reaction; J. of Clin. Microbiology, May 1992, p. 1331–1334.
Reischl,U. et al.; PCR–Based Detection of Mycobacteria in Sputum Samples Using a Simple and Reliable DNA Extraction Protocol; BioTechniques, vol. 17, No. 5 (1995), p. 844–845.
Zambardi, G. et al.; Comparison of three primer sets for the detection of *Mycobacterium tuberculosis* in clinical samples by polymerase chain reaction; Am Biol Clin (1993), 50, p. 893–897.
Folgueira, L. et al.; Detection of *Mycobacterium tuberculosis* DNA in Clinical Samples by Using a Simple Lysis Method and Polymerase Chain Reaction; Journal of Clinical Microbiology, Apr. 1993, p. 1019–1021.

*Primary Examiner*—John Kim

[57] ABSTRACT

The present invention relates to methods for concentrating bacteria from a viscous biological sample. The methods involve adding to the sample a water-soluble, density-lowering agent having a density of 0.7 to 0.9 g/ml and a boiling point greater than 50° C. The invention also relates to methods for concentrating bacteria and free bacterial nucleic acids from a biological sample that involve mixing with the sample a density-lowering agent and a monovalent salt.

15 Claims, No Drawings

USE OF AN ALCOHOL-SALT BUFFER WASH FOR THE EFFICIENT RECOVERY OF MYCOBACTERIA AND MYCOBACTERIAL DNA FROM RESPIRATORY SEDIMENT

This application claims the benefit of U.S. Provisional Application Ser. No. 60/039,239, filed on Feb. 28, 1997.

BACKGROUND OF THE INVENTION

1. Field of the Invention

The present invention relates to methods for concentrating and recovering bacteria and free bacterial nucleic acids from biological samples. In particular, the present invention relates to methods for concentrating *Mycobacterium tuberculosis* in a manner that is compatible with subsequent nucleic acid analysis.

2. Background Information

*Mycobacterium tuberculosis* (Mtb), the causative agent of tuberculosis in humans, is conventionally identified by time-consuming microbiological culture. Clinical specimens submitted for mycobacterial culture are often contaminated with other more rapidly growing microorganisms. These specimens, typically a sputum or other respiratory sample, must be subjected to a digestion-decontamination process to liquefy viscous organic material and eliminate unwanted organisms. The most common reagents used in the digestion-decontamination process are N-acetyl-L-cysteine-sodium hydroxide (NALC—NaOH), sodium hydroxide-sodium dodecyl sulfate (NaOH—SDS) or NaOH alone. A typical digestion-decontamination protocol would include incubating the respiratory sample with one of the above reagents, lowering the pH of the mixture by diluting with buffer solution or water, and centrifuging the mixture to concentrate the mycobacteria in a pellet. A portion of the supernatant would be decanted and the pellet resuspended in the remaining supernatant fluid or in a buffer solution. Suspensions obtained in such a manner are termed "respiratory sediments".

While respiratory sediments are suitable for culture, they are not suitable for nucleic acid analysis, such as nucleic acid amplification, restriction digestion, and nucleotide sequencing. Prior to conducting nucleic acid analysis, it is necessary to remove the digestion-decontamination reagents from the respiratory sediments because these reagents interfere with nucleic acid analysis. It is also useful to further concentrate the mycobacteria from sediment samples having low mycobacteria titers prior to nucleic acid analysis to increase the likelihood of nucleic acid detection.

Prior to the present invention, those skilled in the art attempted to solve the problems of contaminating digestion-decontamination reagents and low bacterial concentrations by diluting the samples in aqueous solutions, further centrifuging to pellet the mycobacteria, and discarding the supernatant solution containing the digestion-decontamination reagents. For example, Beavis et al. (J. Clin. Microbiol., 33, 2582–2586 (1995)) use a method in which 100 $\mu$L of respiratory sediment is mixed with 500 $\mu$L of a specimen wash reagent comprising Tris-HCl and 1% solubilizer. The mycobacteria are pelleted from the mixture by centrifugation at 12,500×g for 10 minutes. (See also, Roche Molecular Systems. 1994. Roche Amplicor *Mycobacterium tuberculosis* test insert, Roche Molecular Systems, Branchburg, N.J.) Such methods, however, have limitations. These methods are not particularly suitable for concentrating bacteria from large sample volumes because addition of the wash buffer increases the volume five-fold. In addition, such methods are limited because mycobacteria are very buoyant and are difficult to pellet from aqueous media. Thus, centrifugation in water or aqueous buffer solution, such as that utilized by Beavis et al., can result in significant loss of the target organisms. In addition, free mycobacterial nucleic acids in the respiratory sediment are not pelleted during centrifugation in aqueous medium. Free nucleic acids exist in the respiratory sediment because they can be released during bacterial lysis caused by digestion and decontamination of fresh samples, and by freezing and thawing of stored respiratory sediments.

The present invention overcomes these problems by providing a method for concentrating bacteria, including *M. tuberculosis*, from viscous biological samples. The present invention also provides a method for concentrating free bacterial nucleic acids as well as the bacteria present in biological samples. Samples processed according to the methods of the present invention can be used for subsequent nucleic acid analysis.

SUMMARY OF THE INVENTION

Thus, it is an object of the present invention to provide a method for concentrating and processing bacteria that removes digestion-decontamination reagents from the sample.

It is another object of the present invention to simultaneously recover both bacteria and any free bacterial DNA present in the biological sample.

It has been unexpectedly found that a water-miscible, density-lowering agent having a density of 0.7 to 0.9 g/ml and a boiling point greater than 50° C. can be used to concentrate bacteria from biological samples. It has also been found that such density-lowering agents can be used in combination with a monovalent salt, such as sodium acetate, to recover intact bacteria and bacterial DNA from biological samples that have a density greater than that of the target bacteria.

In one embodiment, the present invention relates to a method for concentrating bacteria from a viscous biological sample. The method comprises adding to the sample, in an amount sufficient to reduce the density of the sample to less than the density of the bacteria, a water-soluble, density-lowering agent having a density of 0.7 to 0.9 g/ml and a boiling point greater than 50° C., and centrifuging the sample to pellet any bacteria present in the sample.

In another embodiment, the present invention relates to a method for concentrating bacteria and bacterial nucleic acids from a biological sample. The method comprises adding to the sample, in an amount sufficient to reduce the density of the sample to less than the density of the bacteria, a water-soluble, density-lowering agent having a density of 0.7 to 0.9 g/ml and a boiling point greater than 50° C., and, in an amount sufficient to precipitate the free bacterial nucleic acids, a monovalent salt. The sample is then centrifuged to pellet any bacteria and any free bacterial nucleic acids present in the sample.

In a further embodiment, the present invention relates to a method for concentrating bacteria from a viscous biological sample and, simultaneously, adjusting the pH of the sample. The method involves adding to the sample, in an amount sufficient to reduce the density of the sample to less than the density of the bacteria, a water-soluble, density-lowering agent having a density of 0.7 to 0.9 g/ml and a boiling point greater than 50° C., and a pH buffering agent. The sample is then centrifuged to pellet any bacteria present in the sample.

DETAILED DESCRIPTION OF THE INVENTION

Various other objects and advantages of the present invention will be apparent from the detailed description of the invention.

All publications mentioned herein are hereby incorporated by reference.

The present invention provides methods for processing samples for detection and identification of bacteria, such as *Mycobacterium tuberculosis*, that are compatible with nucleic acid based analysis. The present methods are compatible with a variety of nucleic acid analysis procedures, including nucleic acid amplification (such as PCR and ligase chain reaction), restriction digestion, and nucleotide sequencing, because the inhibitory substances employed for digestion-decontamination of the sample are efficiently removed.

In one embodiment, the present invention relates to methods for concentrating bacteria from viscous biological samples. The bacteria contained in a biological sample are concentrated by mixing the sample with a water-miscible, density-lowering agent and then centrifuging the sample to pellet any bacteria present in the sample. The density-lowering agent reduces the density of the resulting mixture to less than that of the bacteria, and thereby, enhances recovery of the bacteria upon centrifugation.

Density-lowering agents suitable for use in the present invention are water-soluble, have a density of 0.7 to 0.9 g/ml, and have a boiling point greater than 50° C. Such agents include, but are not limited to, substituted or unsubstituted methyl alcohols, substituted or unsubstituted ethyl alcohols, substituted or unsubstituted propyl alcohols, and ketones. For example, ethanol, methanol, methyl ethyl ketone, 2-pentanol, 3-pentanone, propanol, isobutyl alcohol, 2-propanol, tert. butyl alcohol, or 2-propanone could be employed as the density-lowering agent in the present invention. Preferably, the density-lowering agent is a substituted or unsubstituted methyl alcohol, substituted or unsubstituted ethyl alcohol, or substituted or unsubstituted propyl alcohol. More preferably, ethanol is used as the density-lowering agent in the methods of the present invention.

The density-lowering agent is added to the sample in an amount sufficient to reduce the density of the sample to less than that of the target bacteria. Such amounts are readily determinable by those skilled in the art. Preferably, 2 to 6 volumes of density-lowering agent are added per unit volume of sample; more preferably, 2 to 2.5 volumes of density-lowering agent are added per unit volume of sample.

In another embodiment, the present invention relates to methods for concentrating bacteria from a viscous biological sample and, simultaneously, adjusting the pH of the sample to a level compatible with subsequent analysis. For example, a buffer such as acetate, citrate, or Tris can be combined with the density lowering agent to wash sputum sediment samples having a pH of 12–14 to lower the pH to a level compatible with polymer capture (pH 6.8) or PCR (pH 8.5). (For a discussion of polymer capture, see U.S. Pat. Nos. 5,582,988, 5,434,270, and 5,523,368.) Bacteria contained in a biological sample are concentrated by mixing the sample with a water-soluble, density-lowering agent and a pH buffering agent. The sample is then centrifuged to pellet any bacteria present in the sample.

In a further embodiment, the present invention relates to methods for concentrating bacteria and free bacterial nucleic acids from biological samples. Bacterial nucleic acids can be released from the bacteria, for example, during storage and freeze-thaw treatments. This free bacterial DNA in the sample can be concentrated and recovered using the present invention. Both bacteria and free bacterial nucleic acids contained in a biological sample are concentrated by treating the sample with a water-soluble, density-lowering agent and a monovalent salt. The density-lowering agent and the monovalent salt may be added to the pellet pre-mixed or individually. The mixture is then centrifuged to pellet bacteria and bacterial nucleic acids that may be present in the sample. The monovalent salt helps to precipitate free DNA from aqueous solution as it provides cations required to counter the negative charge on DNA. The use of a density-lowering agent, such as ethanol or isopropanol, together with a monovalent salt such as an acetate or chloride salt of sodium, potassium, ammonium, or lithium, results in the concentration and recovery of bacteria and free bacterial DNA present in the sample.

Monovalent salts suitable for use in the present invention include, but are not limited to, metal salts of acetate or chloride and non-metal salts of acetate or chloride. Preferably, the monovalent salt is a lithium, sodium, potassium or ammonium salt of acetate or chloride. More preferably, the monovalent salt is sodium acetate, sodium chloride, ammonium acetate, or lithium chloride. The monovalent salt is added in an amount sufficient to precipitate any free bacterial nucleic acids present in the sample. Such amounts are readily determinable by those skilled in the art.

Bacteria that can be concentrated using the methods of the present invention include, but are not limited to, mycobacteria (such as *Mycobacterium tuberculosis* and *Mycobacterium avium*), Prevotella sp., Porphyromonas sp., *Chlamydia trachomatis* sp., *Neisseria gonorrhoeae* sp., Staphylococcus sp., Streptococcus sp., Enterococcus sp., Clostridium sp., and Bacteroides sp. Other detectable species would be readily apparent to one skilled in the art.

Bacteria can be concentrated and recovered using the methods of the present invention from various viscous biological samples including, but not limited to, respiratory samples (such as sputum samples), respiratory sediment, oral fluid, vaginal fluid, seminal fluid, wound infection fluid, and abcess fluid. Preferably, the biological sample is a respiratory sample. More preferably, the respiratory sample is pretreated to obtain a respiratory sediment for use in the present invention.

By way of example, *M. tuberculosis* can be concentrated from a respiratory sediment according to the methods of the present invention. To prepare the respiratory sediment, a respiratory sample, such as sputum, is first processed by conventional procedures for liquification and decontamination. Any of the known digestion-decontamination procedures are suitable for this step including, but not limited to, various modifications of the NALC—NaOH treatment (Kent & Kubica, Public Health Mycobacteriology A Guide for the Level III Laboratory, U.S. Department of Health and Human Services, 31–47(1985); Noordhock et al., J. Clin. Microbiol., 32, 277–284 (1994)). These methods generally include liquifying the sample and killing competing bacteria with a digestion-decontamination reagent and then centrifuging the liquified sample to pellet the bacteria. The respended pellet, the respiratory sediment, can then be processed according to the present invention to concentrate mycobacteria present therein. For example, *M. tuberculosis* can be concentrated from the prepared respiratory sediment using the density-lowering agent ethanol.

To concentrate and recover *M. tuberculosis* and any mycobacterial nucleic acids present in the respiratory sediment, the specimen can be treated with a density-lowering agent such as ethanol, and a monovalent salt such as sodium acetate, according to the methods of the present invention to remove contaminating digestion-decontamination reagents, to concentrate low bacterial titers, and to recover free mycobacterial nucleic acids.

A density-lowering agent together with sodium or ammonium acetate can be utilized to concentrate, wash, and change to a desired value the pH of mycobacterial preparations from respiratory sediment samples, and render them suitable for subsequent nucleic acid detection or analysis such as polymerase chain reaction (PCR) analysis. For nucleic acid detection and/or analysis the recovered mycobacteria present in the pellet are lysed using standard lysing methods well known to those skilled in the art. Suitable lysing methods include, but are not limited to, heating, sonication, bead beating, freeze-thaw; and protease digestion. See, for example, Noordhock et al., J. Clin. Microbiol., 32, 277–284 (1994); Nolte et al., J. Clin. Microbiol., 31, 1777–1782 (1993); Forbes et al., J. Clin. Microbiol., 31, 1688–1694 (1993); Hurley et al., J. Clin. Microbiol., 25, 2227–2229 (1987); and Folgueira et al., J. Clin.

Microbiol., 31, 1019–1021 (1993).

The nucleic acids released from the lysed mycobacteria as well as the recovered free mycobacterial nucleic acids may be used for nucleic acid analysis as the digestion-decontamination reagents have been removed.

The recovered nucleic acids can be used, for example, in nucleic acid hybridization methods and nucleic acid amplification procedures, such as, PCR, ligase chain reaction, nucleic acid sequence based amplification (NASBA), transcription mediated amplification (TMA), strand displacement amplification (SDA), and Q-beta replicase. Such protocols are well known in the art and are readily available to those skilled in the art. For example, the general principles and conditions for amplification and detection of nucleic acids using PCR are quite well known, the details of which are provided in numerous references including U.S. Pat. Nos. 4,683,195, 4,683,202, and 4,965,188, and by Guatelli et al, Clin. Microbiol. Rev., 2 (2), pp. 217–226 (1989). The noted U.S. patents are incorporated herein by reference. In view of the teaching in the art and the specific teaching provided herein, a worker skilled in the art should have no difficulty in practicing the present invention by combining the bacteria concentration and recovery method of this invention with cell lysis and polymerase chain reaction procedures.

The following Examples are provided to illustrate certain embodiments of the present invention, and are not to be construed as limiting the invention.

EXAMPLES

Materials and Methods

Frozen sputum sediments free of or containing *M. tuberculosis* (Mtb) were obtained from several clinical microbiology laboratories.

The following reagents were prepared and used in the experiments. (Deionized water was used in the preparation of all reagents.)

1. Sodium acetate solution (NaAc):

Anhydrous sodium acetate (12.3 g) was dissolved in approximately 40 mL $H_2O$. The pH of the solution was adjusted to 5.2 with glacial acetic acid, and the volume brought to 50 mL with water.

2. Ethanol/sodium acetate reagent (EtOH/NaAc):

One part by volume of the above sodium acetate solution was combined with 20 to 25 parts by volume ethanol. Both 200 proof (punctilious) ethanol and denatured ethanol (containing 5% isopropanol and 5% methanol) were used with similar success.

Method 1

NaAc and EtOH Added Separately to Sputum Sediment Sample

One part by volume of the above-described NaAc solution was pipetted into a 1.5 mL microcentrifuge tube. Ten parts by volume of sputum sediment was added and the solution was vortexed briefly to mix. Twenty to twenty-five parts by volume of ethanol was added, and the solution was vortexed again briefly to mix. The microcentrifuge tube containing the sample was then placed in a microcentrifuge and spun at 16,000×g for 15 minutes to pellet bacteria and precipitate nucleic acids, and the supernatant was discarded.

For further processing, bacterial/DNA pellets were resuspended in lysis reagent (10 mM Tris, pH 8.0, 1% Tween 20, 1% Triton X-100, 0.1% sodium dodecyl sulfate) and heated at 100° C. for 30 min to lyse bacteria and release DNA. DNA was recovered from these lysates by the polymer capture technique, as described in U.S. Pat. No. 5,582,988. Briefly, a soluble, weakly basic cationic polymer is used. DNA binds electrostatically to the polymer via its negatively charged phosphate groups, and forms an insoluble complex. The complex is pelleted by centrifugation, the supernatant is discarded, and the purified DNA is released by heating in alkaline solution.

Recovered mycobacterial DNA was amplified and detected using a Johnson & Johnson Clinical Diagnostics, Inc. pouch containment system for PCR nucleic acid amplification and detection as described in U.S. Pat. Nos. 5,089,233, 5,229,297 and 5,380,489. Briefly, sample plus PCR reagents were mixed and loaded into a blister of the plastic pouch, then the pouch is sealed. Biotin-labeled oligonucleotides, representing DNA sequences unique to MTb, are used to prime amplification of MTb-specific DNA with thermally stable DNA polymerase. Reaction mixtures containing sample, the DNA polymerase, dNTP's, buffer and salt are first heated to denature DNA, then cycled back and forth from high temperature (95° C.) to denature and lower temperature (65–75° C.) to anneal primers and extend or synthesize copies of the DNA sequence. Amplified target is detected after reaction products are forced through a detection chamber, where they hybridize with complementary oligos attached to beads. The hybridized product is detected after HRP-streptavidin and subsequently an HRP-dye substrate are forced through the detection chamber.

Method 2

NaAc/EtOH Combined Reagent Mixed with Sputum Sediment Sample

Twenty to twenty-five parts by volume of the combined EtOH/NaAc reagent was pipetted into a microcentrifuge tube. Ten parts by volume of sputum sediment sample was added, and the solution was vortexed briefly to mix. The microcentrifuge tube containing the sample was then placed in a microcentrifuge and spun at 16,000×g for 15 minutes to pellet bacteria and precipitated nucleic acids, and the supernatant was discarded.

For further processing, bacterial/DNA pellets were resuspended in lysis reagent (10 mM Tris, pH 8.0, 1% Tween 20, 1% Triton X-100, 0.1% sodium dodecyl sulfate) and heated at 100° C. for 30 min to lyse bacteria and release DNA. DNA was recovered from these lysates by the polymer capture technique, as described in U.S. Pat. No. 5,582,988.

Recovered mycobacterial DNA was amplified and detected using a Johnson & Johnson Clinical Diagnostics, Inc. pouch containment system for PCR nucleic acid amplification and detection as described in U.S. Pat. Nos. 5,089,233, 5,229,297 and 5,380,489.

Example 1
Effects of pH, Salt, Alcohol, and Temperature on Precipitation and Recovery of Free DNA To identify optimum conditions for recovery of free DNA from solution over the pH range found in sputum sediment and other respiratory sediment samples, water was adjusted to pH 7, 10, or 14 with sodium hydroxide to simulate the pH range of respiratory sediments, and used to dilute calf thymus DNA (Ct-DNA), obtained from Sigma Chemical Co., to a final concentration of 50 ng DNA/$\mu$L. Either sodium chloride (NaCl) or sodium acetate (NAAC) was added to each pH adjusted DNA sample to give final concentrations of 0.2M NaCl or 0.3M NaAc. One half milliliter aliquots were transferred to microcentrifuge tubes, mixed with either 1 mL of ethanol (EtOH) or 0.5 mL of isopropanol (IPP), and either immediately centrifuged at ambient room temperature (RT) or incubated at $-20°$ C. for 1 hr before centrifugation. Centrifugation was at 16,000×g for 15 minutes. Pelleted material was resuspended in 0.5 mL of water, and its absorption at 260 nm, the $\lambda$max for DNA, was measured with a spectrophotometer and compared with the absorption of the unprecipitated material. The percent recovery of DNA for the different experimental conditions is presented below in Table 1.

TABLE 1

Effects of pH, Salt, Alcohol, and Incubation at $-20°$ C. on Recovery of DNA

| | | | salt = NaCl | salt = NaAc | |
|---|---|---|---|---|---|
| pH of DNA soln | alcohol | incubation | % recovery | % recovery | std dev (n = 3) |
| 7 | EtOH | NONE | 13 | 120 | 0 |
|   | EtOH | 1 h, −20 | 15 | 120 | 2 |
|   | IPP | NONE | 12 | 117 | 1 |
|   | IPP | 1 h, −20 | 86 | 118 | 0 |
| 10 | EtOH | NONE | 16 | 120 | 1 |
|    | EtOH | 1 h, −20 | 20 | 119 | 1 |
|    | IPP | NONE | 22 | 118 | 0 |
|    | IPP | 1 h, −20 | 54 | 113 | 4 |
| 14 | EtOH | NONE | 6 | 93 | 1 |
|    | EtOH | 1 h, −20 | 5 | 92 | 0 |
|    | IPP | NONE | 2 | 6 | 3 |
|    | IPP | 1 h, −20 | 2 | 75 | 3 |

The results show that NaAc combined with either EtOH or IPP is effective in allowing quantitative recovery of DNA from samples at pH 7 or 10, whether centrifuged immediately or after incubating at $-20°$ C. Even at pH 14, the recovery of DNA with a NaAc and EtOH combination was nearly quantitative, but IPP in combination with NaAc was less effective at this pH. The combination of NaCl and alcohol did not allow efficient recovery of Ct-DNA under any of the conditions tested. Therefore, the combination of NaAc with EtOH and immediate centrifugation after mixing with the sample at ambient temperature are preferred for use with sputum sediment and other respiratory sediment samples.

Example 2
Recovery of M. Tuberculosis (Mtb) from Sputum Sediment

In this experiment, the recovery of Mtb from sputum sediment samples was shown to be more efficient if the samples are first diluted with either EtOH alone or NaAc and EtOH together. Cultured Mtb were added to aliquots of a pool of mixed respiratory sediments to obtain several different titers, expressed in colony forming units (CFU) per PCR assay, and NaAc/EtOH treatment was performed according to Method 1 described above. Two hundred $\mu$L aliquots were treated as indicated in Table 2. For EtOH only, NaAc was omitted from the wash. For spin only, the wash was omitted entirely, that is, the respiratory sediment alone, without EtOH or NaAc, was centrifuged as for the first two treatments. The pelleted samples were further processed and assayed for Mtb by PCR as outlined above. A no-spin control, for which lysis reagent was added directly to the uncentrifuged respiratory sediment, was included to show maximum recovery. Although many respiratory sediment specimens interfere with polymer capture or PCR when used without an ethanol wash, this particular sample was chosen for the no-spin control because it did not interfere. Values given in Table 2 are percentage of replicates that were PCR positive for Mtb; n=4 (*n=3; **n=1).

The results shown in Table 2 indicate that cultured bacteria pellet more efficiently from respiratory sediments in a medium containing EtOH or NaAc/EtOH than with direct centrifugation in the sputum sediment without EtOH (spin only). The respiratory sediment pool used was contaminated with a very small number of Mtb organisms, not detected by culture, accounting for the occasional PCR positive result in the zero CFU set.

TABLE 2

Recovery of Cultured Mtb from Pooled Sputum Sediment

| | Treatment | | | |
|---|---|---|---|---|
| Mtb (CFU) | NaAc + EtOH | EtOH only | Spin only | No spin |
| 0 | 0% | 25% | 0% | 25% |
| 2 | 75% | 100% | 0% | 100% |
| 5 | 100% | 100% | 50% | 100% |
| 10 | 100% | 100% | 50% | 100% |
| 50 | 100% | 100% | 75% | 100% |
| 100 | 100% | 100% | 100% | 100%** |

Example 3

Recovery of Mtb from Patient Samples

This experiment was identical to that in Example 2 except that the source of Mtb was actual patient samples rather than culture. A pool of respiratory sediment samples that had tested positive for Mtb by culture was diluted with a pool of respiratory sediment samples that tested negative for Mtb by culture. Two hundred microliter aliquots were treated as in Example 2. Values given are percentage of replicates PCR positive for Mtb; n=4. As in Example 2, the culture-negative pool contained levels of Mtb that were detected by PCR. Therefore, any differences between washes with and without NaAc were not observed. Nonetheless, a loss of target was detected for samples pelleted without ethanol or sodium acetate (spin only).

TABLE 3

Recovery of Mtb from Patient Samples

| Dilution of Mtb + pool | Treatment | | | |
|---|---|---|---|---|
| | NaAc + EtOH | EtOH only | Spin only | No spin |
| "neg" pool | 100% | 100% | 50% | 100% |
| $10^{-7}$ | 100% | 100% | 25% | 100% |
| $10^{-6}$ | 100% | 100% | 75% | 100% |
| $10^{-5}$ | 100% | 100% | 25% | 100% |
| $10^{-4}$ | 100% | 100% | 100% | 100% |
| $10^{-3}$ | 100% | 100% | 100% | 100% |

Example 4
Comparison of Pure and Denatured Ethanol

It may be advantageous to use denatured ethanol instead of pure ethanol because of cost and regulatory issues. Therefore, efficacy of recovery of cultured mycobacteria from a respiratory sediment pool with pure ethanol (200 proof) and denatured ethanol (90% ethanol, 5% methanol, 5% isopropanol) was compared. Test samples were prepared and treated with NaAc and EtOH as in Example 2, but denatured ethanol was substituted for pure ethanol in one set of samples. Values given are percentage of replicates PCR positive for Mtb; n=6. As in Examples 2 and 3, the culture-negative pool is slightly contaminated with Mtb, however, the results are identical for pure and denatured ethanol.

TABLE 4

Comparison of Pure Ethanol and Denatured Ethanol

| Mtb (CFU) | Pure Ethanol | Denatured Ethanol |
|---|---|---|
| 0 | 17% | 17% |
| 0.5 | 83% | 83% |
| 1 | 100% | 100% |
| 2 | 100% | 100% |
| 5 | 100% | 100% |
| 10 | 100% | 100% |

Example 5
Comparison of EtOH alone with EtOH/NaAc

This experiment demonstrates that NaAc together with EtOH provide for more efficient recovery and detection of mycobacteria from a subset of sputum sediment samples. Test samples were prepared and treated with NaAc/EtOH or EtOH alone, as in Example 2, except that a different, PCR-negative pool of respiratory sediment was used, the volume of respiratory sediment was increased to 300 µL, and 700 µL of the combined EtOH/NaAc reagent (described in method 2 above) was used. Values given in Table 5 are percentage of the replicates that were PCR positive for Mtb; n=4. As shown, ethanol and sodium acetate together were more effective than ethanol alone. Subsequent experiments demonstrated that DNA was recovered efficiently by polymer capture when NaAc was included with the ethanol treatment. Efficient polymer capture required a pH very close to 6.8. The pH of some respiratory samples was 7.4 during polymer capture if NaAc was omitted from the ethanol wash, and DNA was not captured efficiently. However, the pH with a second aliquot of these same samples was 6.8 to 7.1 if NaAc was included with the EtOH, and DNA was captured efficiently. It is evident that addition of NaAc adjusts the pH, and thereby, improves recovery of Mtb DNA from this subset of clinical samples.

TABLE 5

Comparison of EtOH alone with EtOH/NaAc

| Mtb (CFU) | EtOH alone | EtOH/ NaAc |
|---|---|---|
| 0 | 0% | 0% |
| 0.25 | 0% | 25% |
| 0.5 | 25% | 75% |
| 1 | 50% | 100% |
| 2 | 0% | 100% |
| 5 | 25% | 100% |

Example 6
Detection of free Mtb DNA in Sputum Sediment Samples After Freeze-Thaw This experiment demonstrates the presence of free Mtb DNA in previously frozen sputum sediments. Three 200 µL aliquots of culture-positive sputum sediment samples, prepared as in Example 3, were centrifuged without addition of EtOH/NaAc. The resulting supernatants were passed through 0.2 µm filters to remove residual bacteria. Both the filtered supernatants, which would contain any free Mtb DNA, and the pellets, which would contain intact Mtb, were processed further and assayed for Mtb DNA by PCR as described above. Table 6 shows the percentage of replicates (n=4) that were PCR positive for Mtb DNA. The data indicate that there is significant free Mtb DNA in this sputum sediment sample, as much as ten fold greater than the amount recovered from intact Mtb organisms. As shown here and in Example 1, free DNA can be recovered with the method of the present invention.

TABLE 6

Mtb DNA Detected in Respiratory Sediment Pellet and Filtrate Without Wash

| Dilution | Pellet | Filtrate |
|---|---|---|
| $10^{-7}$ | 0% | 0% |
| $10^{-6}$ | 0% | 0% |
| $10^{-5}$ | 0% | 100% |
| $10^{-4}$ | 100% | 100% |
| $10^{-3}$ | 100% | 100% |
| $10^{-2}$ | 100% | 100% |
| $10^{-1}$ | 100% | 100% |

While the foregoing invention has been described in some detail for purposes of clarity and understanding, it will be clear to one skilled in the art from a reading of this disclosure that various changes in form and detail can be made without departing from the true scope of the invention.

What is claimed:

1. A method for concentrating bacteria and free bacterial nucleic acids from a biological sample comprising:
   a) adding to the sample, in an amount sufficient to reduce the density of the sample to less than the density of the bacteria, a water-soluble, density-lowering agent having a density of 0.7 to 0.9 g/ml and a boiling point greater than 50° C., and in an amount sufficient to precipitate the free bacterial nucleic acids, a monovalent salt; and
   b) centrifuging the sample to pellet any bacteria and any free bacterial nucleic acids present in the sample.

2. The method according to claim 1 wherein the sample is pretreated with reagents that interfere with nucleic acid analysis.

3. The method according to claim 2 wherein the sample is a respiratory sediment.

4. The method according to claim 1 wherein the biological sample is selected from the group consisting of: respiratory sample, respiratory sediment, oral fluid, vaginal fluid, seminal fluid, wound infection fluid, and abcess fluid.

5. The method according to claim 1 wherein the density-lowering agent is selected from the group consisting of: substituted or unsubstituted methyl alcohol, substituted or unsubstituted ethyl alcohol, substituted or unsubstituted propyl alcohol, and ketones.

6. The method according to claim 1 wherein the density-lowering agent is selected from the group consisting of: substituted or unsubstituted methyl alcohol, substituted or unsubstituted ethyl alcohol, and substituted or unsubstituted propyl alcohol.

7. The method according to claim 6 wherein the density-lowering agent is ethanol.

8. The method according to claim 1 wherein 2 to 6 volumes of the density-lowering agent per unit volume of sample is added.

9. The method according to claim 8 wherein 2 to 2.5 volumes of the density-lowering agent per unit volume of sample is added.

10. The method according to claim 1 wherein the bacteria is selected from the group consisting of: Mycobacterium sp., Prevotella sp., Porphyromonas sp., *Chlamydia trachomatis* sp., *Neisseria gonorrhoeae* sp., Staphylococcus sp., Streptococcus sp., Enterococcus sp., Clostridium sp., and Bacteroides sp.

11. The method according to claim 10 wherein the bacteria is selected from the group consisting of: *Mycobacterium tuberculosis* complex and *Mycobacterium avium* complex.

12. The method according to claim 1 wherein the monovalent salt is selected from the group consisting of sodium acetate, sodium chloride, ammonium acetate, and lithium chloride.

13. The method according to claim 1 wherein the bacteria is *Mycobacterium tuberculosis*, the viscous biological sample is respiratory sediment, the density-lowering agent is ethanol, and the monovalent salt is sodium acetate.

14. A method for concentrating bacteria from a viscous biological sample comprising:
  a) adding to the sample in an amount sufficient to reduce the density of the sample to less than the density of the bacteria a water-soluble, density-lowering agent having a density of 0.7 to 0.9 g/ml and a boiling point greater than 50° C., and a pH buffering agent; and
  b) centrifuging the sample to pellet any bacteria present in the sample.

15. The method according to claim 14 wherein the pH buffering agent brings the pH of the sample to between 6 and 9.

* * * * *